(12) United States Patent
Nandakumar et al.

(10) Patent No.: US 12,357,753 B2
(45) Date of Patent: Jul. 15, 2025

(54) PRESSURE ACTUATED FLOW CONTROL DEVICE FOR GRAVITY IV SETS

(71) Applicant: CareFusion 303, Inc., San Diego, CA (US)

(72) Inventors: Sridhaar Nandakumar, Chennai (IN); Rahul Puthukkad, Bangalore (IN)

(73) Assignee: CareFusion 303, Inc., San Diego, CA (US)

( * ) Notice: Subject to any disclaimer, the term of this patent is extended or adjusted under 35 U.S.C. 154(b) by 38 days.

(21) Appl. No.: 18/239,646

(22) Filed: Aug. 29, 2023

(65) Prior Publication Data

US 2023/0398292 A1 Dec. 14, 2023

Related U.S. Application Data

(63) Continuation of application No. 17/025,948, filed on Sep. 18, 2020, now Pat. No. 11,771,826.

(51) Int. Cl.
*A61M 5/168* (2006.01)
*A61M 5/14* (2006.01)
(Continued)

(52) U.S. Cl.
CPC .... *A61M 5/16881* (2013.01); *A61M 5/16804* (2013.01); *A61M 5/1411* (2013.01);
(Continued)

(58) Field of Classification Search
CPC .......... A61M 5/16881; A61M 5/16804; A61M 39/22; A61M 39/223; A61M 2039/224;
(Continued)

(56) References Cited

U.S. PATENT DOCUMENTS

| | | |
|---|---|---|
| 2,634,743 A | 4/1953 | Pierre |
| 3,633,606 A | 1/1972 | Hay |

(Continued)

FOREIGN PATENT DOCUMENTS

WO   WO-2018075390 A1   4/2018

OTHER PUBLICATIONS

International Search Report and Written Opinion for Application No. PCT/US2021/050539, dated Dec. 22, 2021, 15 pages.

(Continued)

*Primary Examiner* — Nilay J Shah

(57) ABSTRACT

A flow control device includes a housing having a primary valve body defining a primary inlet and an outlet, a secondary valve body defining a secondary inlet and a chamber defined by an inner circumferential surface of the housing and fluidly connecting the primary and secondary inlets with the outlet. The primary and secondary inlets share a common central axis perpendicularly disposed to a central axis of the outlet. A valve member is reciprocally mounted in the chamber to block fluid communication between the secondary inlet and the outlet when fluid pressure into the primary inlet is higher than fluid pressure into the secondary inlet, and block fluid communication between the primary inlet and the outlet when fluid pressure into the secondary inlet is higher than fluid pressure into the primary inlet.

10 Claims, 6 Drawing Sheets

(51) Int. Cl.
    *A61M 5/142* (2006.01)
    *A61M 39/22* (2006.01)
    *A61M 39/24* (2006.01)
(52) U.S. Cl.
    CPC ....... *A61M 5/142* (2013.01); *A61M 2039/224* (2013.01); *A61M 2039/244* (2013.01); *A61M 2039/2473* (2013.01)
(58) Field of Classification Search
    CPC .. A61M 2039/2406; A61M 2039/2413; A61M 5/1408; A61M 5/3294; A61M 5/1407; A61M 5/16827; A61M 5/1409; A61M 2039/2493; A61M 5/19; F16K 11/044; F16K 11/048; F16K 3/00; F16K 3/265; F16K 11/00; F16K 11/02; F16K 11/022; F16K 11/065; F16K 11/06; F16K 3/184; F16K 3/205
    See application file for complete search history.

(56) References Cited

U.S. PATENT DOCUMENTS

| | | |
|---|---|---|
| 4,237,880 A | 12/1980 | Genese |
| 8,171,951 B2 | 5/2012 | Quendt |
| 2007/0272311 A1 | 11/2007 | Trocki et al. |
| 2008/0172006 A1 | 7/2008 | Hicks |
| 2010/0032036 A1* | 2/2010 | Quendt ................ F15B 13/028 235/201 ME |
| 2019/0232041 A1 | 8/2019 | Spohn |
| 2020/0378506 A1 | 12/2020 | Woods |

OTHER PUBLICATIONS

Alanto, "EPDM Material Density | EPDM Sponge Properties | Alanto", Alanto cellular foam solutions, Alanto Ltd, retrieved from the internet: https://www.alanto.co.uk/latest/new/epdm-sponge-properties-densities-and-applications, last retrieved Apr. 7, 2023.
Caple, Carita, RN, BSN, MSHS, "Automatic Intravenous 'Piggy-back': Setting Up", Nursing Practice & Skill, Cinahl Information Systems, Glendale, CA, Aug. 14, 2015, 5 pages.
National Institutes of Health Clinical Center Nursing and Patient Care Services, Procedure: Backflow Technique for Administration of Secondary Intravenous (IV) Solutions, National Institutes of Health Clinical Center Nursing and Patient Care Services, May 19, 2011, 4 pages.
Parafix, "Medical Grade Foam", Parafix Engineered Adhesive Solutions, retrieved from the internet: https://parafix.com/product-groups/medical-grade-materials/medical-grade-foam/, last retrieved Apr. 7, 2023.
Spongerubberballs.com, "Sponge Rubber Balls", 2019, retrieved from the internet: https://web.archive.org/web/20191230030126/http://www.spongerubberballs.com/sponge-rubber-rollers/sponge-rubber-balls/.

* cited by examiner

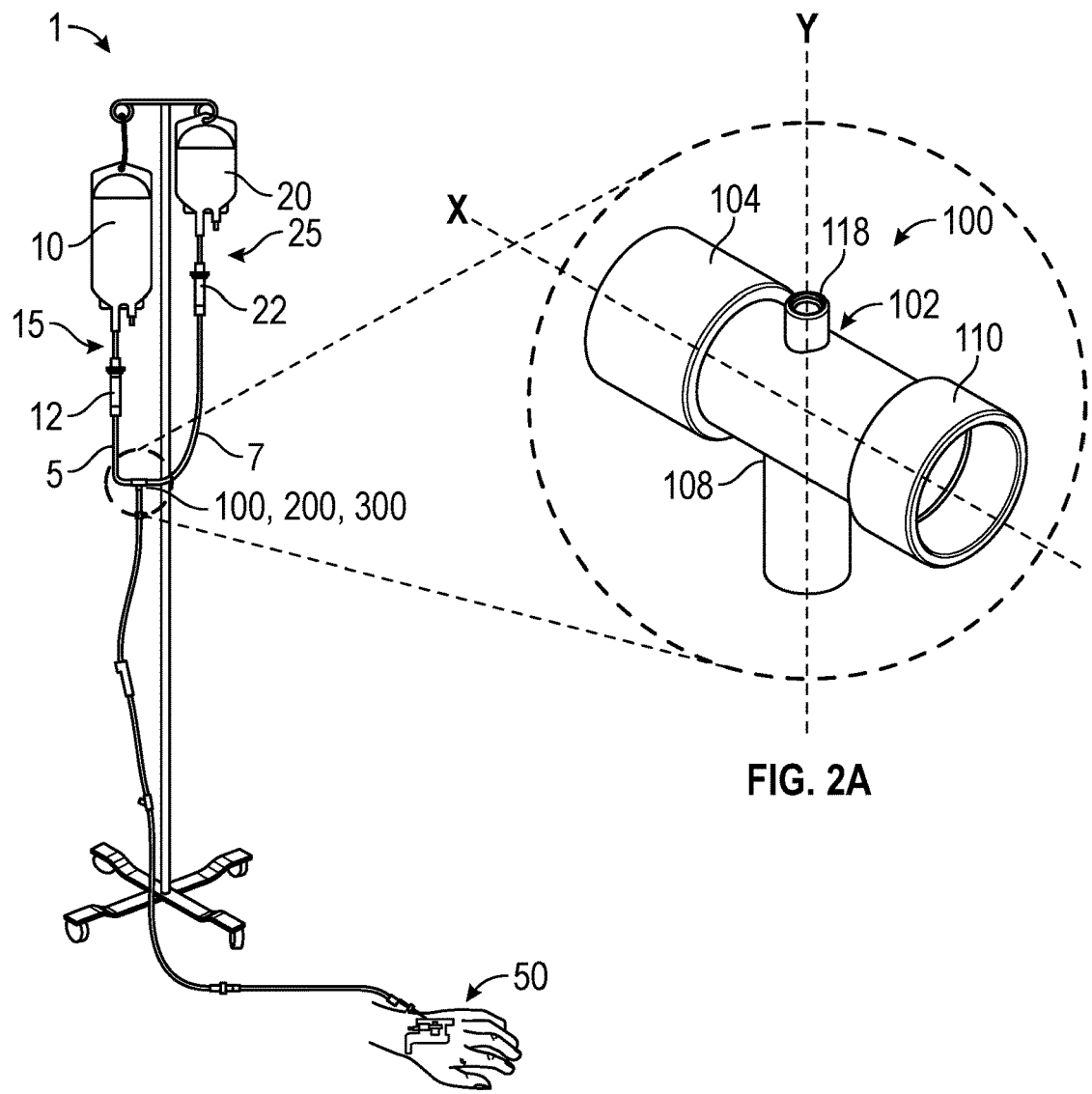
FIG. 2A
FIG. 1
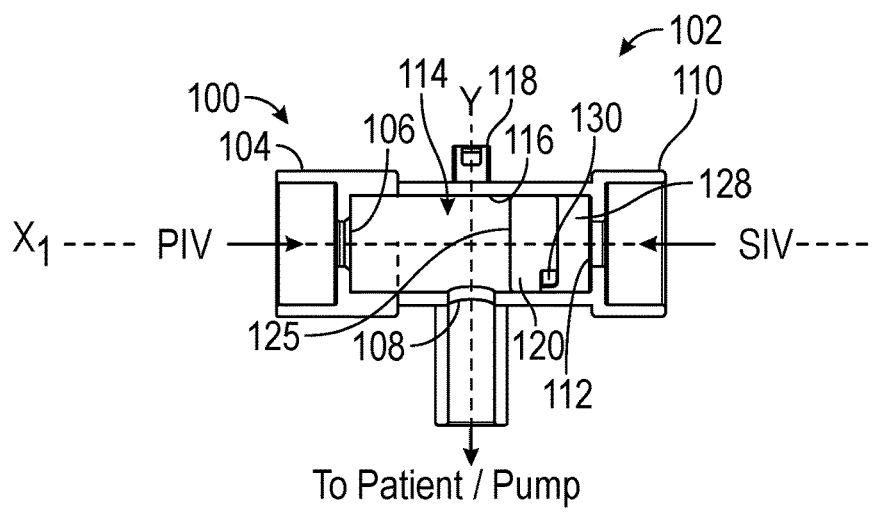
FIG. 2B

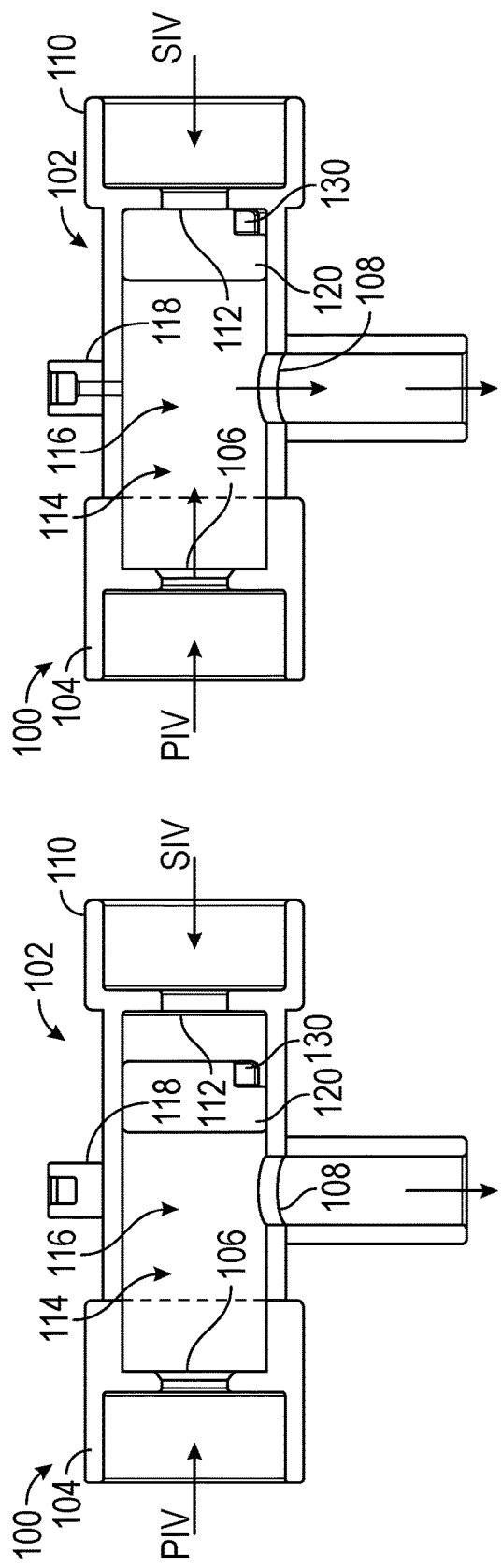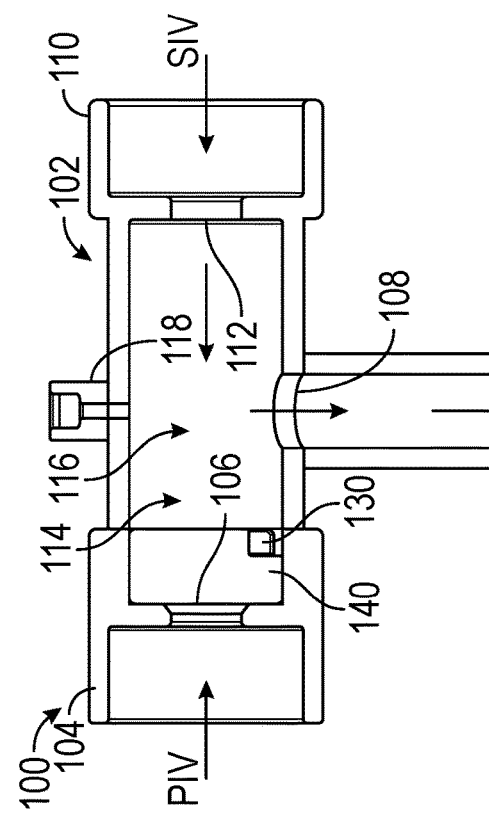

PRESSURE ACTUATED FLOW CONTROL DEVICE FOR GRAVITY IV SETS

CROSS-REFERENCE TO RELATED APPLICATIONS

This application is a continuation of U.S. patent application Ser. No. 17/025,948, filed Sep. 18, 2020, issued as U.S. Pat. No. 11,771,826 on Oct. 3, 2023, entitled "PRESSURE ACTUATED FLOW CONTROL DEVICE FOR GRAVITY IV SETS," which is herein incorporated by reference in its entirety.

TECHNICAL FIELD

The present disclosure generally relates to flow control devices, and more particularly to flow control devices having a valve member capable of preventing under-infusion in IV sets with a secondary line, as well as preventing backflow of drug from the secondary line into the primary line.

BACKGROUND

Infusion IV sets are generally used in infusion therapy in order to deliver medication from a pre-filled container, e.g., an IV bottle or bag containing the desired medication, to a patient. Generally, the IV tubing is connected to a catheter and inserted into the localized area to be treated. In some cases, there is a need to deliver multiple medications to the patient in potentially differing dosages, thereby causing the need for an IV extension set having multiple branches of tubings or fluid lines through which the multiple medications may be dispensed to the patient.

Patients are commonly injected with IV solutions that are initially provided in the IV bottle or bag and dripped into the vein of the patient through an IV line. A flow control device, for example, a check valve, is also commonly included in the IV line to permit fluid flow only in the direction of the patient. This ensures that the medication flows downstream toward the patient, not upstream toward the IV bottle or bag.

During infusion with IV sets, a secondary drug feed could potentially flow backwards into primary IV line leading to under infusion of the secondary drug. Though a check valve may be positioned in the primary line to prevent backflow, check valves are prone to frequent failure. A common reason for check valve failure is due to debris existing in infusates. Additionally, under-infusion frequently occurs due to low pressure difference on either sides of the diaphragm within back check valve which prevents the back check valve to close completely allowing back flow.

The description provided in the background section should not be assumed to be prior art merely because it is mentioned in or associated with the background section. The background section may include information that describes one or more aspects of the subject technology.

SUMMARY

According to various embodiments of the present disclosure, a flow control device may include a housing including a primary inlet, a primary outlet, a secondary inlet, and a secondary outlet, wherein the primary and secondary inlets share a common central axis that is perpendicularly disposed relative to central axes of the primary and secondary outlets; a chamber defined by an inner circumferential surface of the housing, the chamber extending between the primary and secondary inlets for fluidly connecting the primary inlet with the primary outlet and the secondary inlet with the secondary outlet; and a valve member reciprocally mounted in the chamber to (i) block fluid communication between the secondary inlet and the secondary outlet when fluid pressure into the primary inlet is higher than fluid pressure into the secondary inlet, and (ii) block fluid communication between the primary inlet and the primary outlet when fluid pressure into the secondary inlet is higher than fluid pressure into the primary inlet.

It is understood that other configurations of the subject technology will become readily apparent to those skilled in the art from the following detailed description, wherein various configurations of the subject technology are shown and described by way of illustration. As will be realized, the subject technology is capable of other and different configurations and its several details are capable of modification in various other respects, all without departing from the scope of the subject technology. Accordingly, the drawings and detailed description are to be regarded as illustrative in nature and not as restrictive.

BRIEF DESCRIPTION OF THE DRAWINGS

The following figures are included to illustrate certain aspects of the embodiments, and should not be viewed as exclusive embodiments. The subject matter disclosed is capable of considerable modifications, alterations, combinations, and equivalents in form and function, as will occur to those skilled in the art and having the benefit of this disclosure.

FIG. 1 illustrates an IV extension set that includes a flow control device, in accordance with some embodiments of the present disclosure.

FIG. 2A illustrates a perspective view of a flow control device, in accordance with some embodiments of the present disclosure.

FIG. 2B illustrates a cross-sectional view of the flow control device and valve member of FIG. 2A, in accordance with some embodiments of the present disclosure.

FIG. 3A is a cross-sectional view illustrating a flow control device and valve member before coupling to fluid lines of an IV set, in accordance with some embodiments of the present disclosure.

FIG. 3B is a cross-sectional view illustrating the flow control device and valve member of FIG. 3A when coupled to primary and secondary fluid lines of an IV set, where fluid pressure in the primary line is higher than that in the secondary line, in accordance with some embodiments of the present disclosure.

FIG. 3C is a cross-sectional view illustrating the flow control device and valve member of FIG. 3A when coupled to primary and secondary fluid lines of an IV set, where fluid pressure in the secondary line is higher than that in the primary line, in accordance with some embodiments of the present disclosure.

DETAILED DESCRIPTION

Figure 2C:
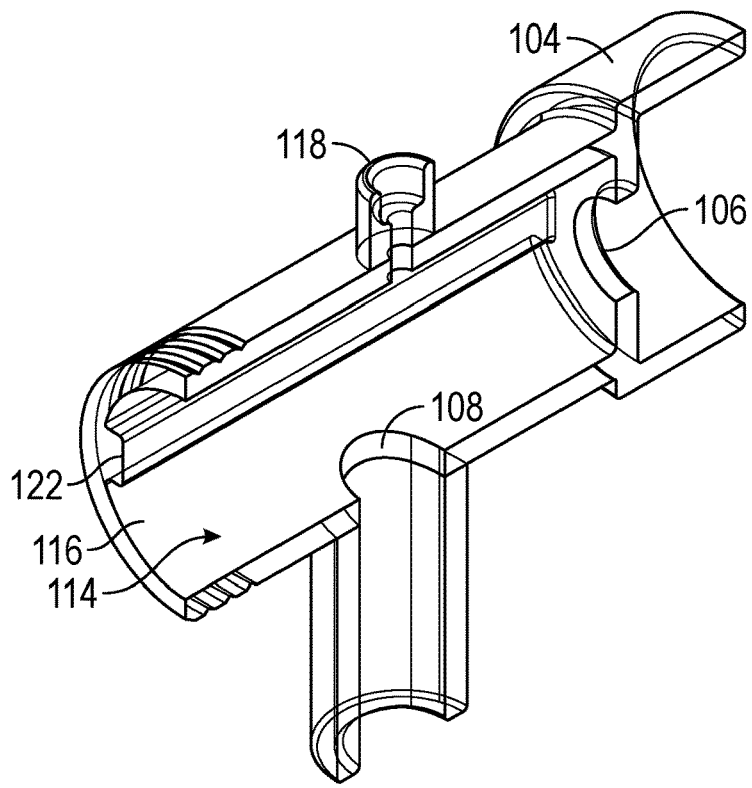
FIG. 2C illustrates a partial cross-sectional view of a housing of the flow control device of FIG. 2A in accordance with some embodiments.

The detailed description set forth below describes various configurations of the subject technology and is not intended to represent the only configurations in which the subject technology may be practiced. The detailed description includes specific details for the purpose of providing a thorough understanding of the subject technology. Accordingly, dimensions may be provided in regard to certain aspects as non-limiting examples. However, it will be apparent to those skilled in the art that the subject technology may be practiced without these specific details. In some instances, well-known structures and components are shown in block diagram form in order to avoid obscuring the concepts of the subject technology.

It is to be understood that the present disclosure includes examples of the subject technology and does not limit the scope of the appended claims. Various aspects of the subject technology will now be disclosed according to particular but non-limiting examples. Various embodiments described in the present disclosure may be carried out in different ways and variations, and in accordance with a desired application or implementation.

The present description relates in general to flow control devices, and more particularly to flow control devices having a valve member capable of preventing under infusion in IV sets with a secondary line, as well as preventing backflow of drug from the secondary line into the primary line.

IV sets with a secondary line tend to experience under infusion of the secondary drug due to failure of the check valve in the primary line. The most frequent causes of failure of the check valve are due to debris accumulated at the time of spiking and seeping of drug in the secondary line into the primary line at low pressures. A common cause of under-infusion is dilution of drug at the time of back priming of the secondary IV and also at the time of equal head in the primary and secondary lines. Other causes include dead volume in the secondary line, as well as time taken to infuse the drug. The flow control devices of the various embodiments described herein overcome the above issues commonly associated with IV sets having primary and secondary lines.

FIG. 1 illustrates a multiple line IV extension set 1 that includes a flow control device 100, 200, 300, in accordance with some embodiments of the present disclosure. IV set 1 includes a primary fluid system 15 and a secondary fluid system 25. An IV pump (not shown) receives fluid from primary fluid system 15 and secondary fluid system 25 via a primary IV line 5 and may control and dispense the fluids therefrom to a patient 50.

In some embodiments, primary fluid system 15 may include a primary fluid source such as a primary fluid bag 10, which may include or contain saline solution or other medicinal fluid or drug to be administered to the patient 50. As illustrated, primary IV line 5 carries primary fluid from a drip chamber 12 to flow control device 100, 200, 300. As shall be described further with respect to the following figures, flow control device 100, 200, 300 may be disposed in primary IV line 5 and allow fluid flow from primary fluid bag 10 to the IV pump (not illustrated) while preventing reverse flow (backflow) of fluid from secondary fluid system 25 toward primary fluid bag 10. In accordance with some embodiments, secondary fluid system 25 includes secondary fluid source such as a secondary fluid bag 8, which may contain drugs or other secondary fluid to be supplied to the patient 50 for treatment. As depicted, the IV set 1 may further include a secondary IV line 7, which carries flow from drip chamber 22 to the flow control device 100, 200, 300.

FIG. 2A a perspective view of a flow control device, in accordance with some embodiments of the present disclosure. FIG. 2B illustrates a cross-sectional view of the flow control device and valve member of FIG. 2A, in accordance with some embodiments of the present disclosure. Referring to FIGS. 2A and 2B, the flow control device 100 may have a housing 102 including a primary valve body 104 and a secondary valve body 110, a chamber 114 interposed between the primary and secondary valve bodies 104 and 110, a vent port 118, and a valve member 120 reciprocally mounted in the chamber 114. As depicted, the primary valve body 104 and secondary valve body 110 may be two components coupled to each other. However, the various embodiments of the present disclosure are not limited to the aforementioned configuration. In some embodiments, the primary valve body 104 and the secondary valve body 110 may be integrally formed as a single unit. For example, the primary valve body 104 and the secondary valve body 110 may be integrally formed as a single tubular housing 102.

As depicted, the primary valve body 104 may define a primary inlet 106 and an outlet 108 of the flow control device 100. The outlet 108 may define a fluid path through which medication or drugs from the primary and secondary inlets may be delivered to the patient 50. The secondary valve body 110 may define a secondary inlet 112 of the flow control device 100. The primary and secondary inlets 106 and 112 may share a common central axis $X_1$. The primary inlet 106 may fluidly communicate the primary IV line 5 with the chamber 114. Similarly, the secondary inlet 112 may fluidly communicate the secondary IV line 7 with the chamber 114. The outlet 108 may have a central axis Y, and the central axis Y may be perpendicularly disposed relative to the common central axis $X_1$ of the primary and secondary inlets 106 and 112.

Referring to FIG. 2B, the flow control device 100 is displayed in cross-sectional view to more clearly illustrate some of the features of the valve member 120. As depicted, the flow control device 100 may be in the form of a housing 102 having an axially extending body defining a central longitudinal axis X. The housing 102 may be generally cylindrical (or tubular) or may have any other shape with a hollow interior capable of defining the chamber 114. The chamber 114 may be defined by an inner circumferential surface 116 of the housing 102. As depicted, the chamber 114 may extend between the primary and secondary valve bodies 104 and 110 to fluidly connect the primary and secondary inlets 106 and 112 with the outlet 108.

FIG. 2C illustrates a partial cross-sectional view of a housing 102 of the flow control device of FIG. 2A in accordance with some embodiments. Referring to FIG. 2C with continued reference to FIG. 2B, the housing 102 may include at least one guide rail 122 extending longitudinally along the inner circumferential surface 116 in the chamber 114. As depicted, the guide rail 122 may be oriented projecting radially inwards towards the central longitudinal axis $X_1$ of the housing 102. In some embodiments, the inner circumferential surface 116 may have more than one guide rail 122 protruding therefrom. For example, two guide rails 122 may protrude from the inner circumferential surface 116 at positions mirroring each other. The two guide rails 122 may be symmetrically disposed about the central longitudinal axis $X_1$ of the inner circumferential surface 116 defining the chamber 114. As shall be described in further detail below, the guide rails 122 may act as a guide so that the valve member 120 may be displaced or otherwise translated axially in the chamber 114 without rotation about its central axis $X_2$ (illustrated in FIG. 2D).

Figure 2D:
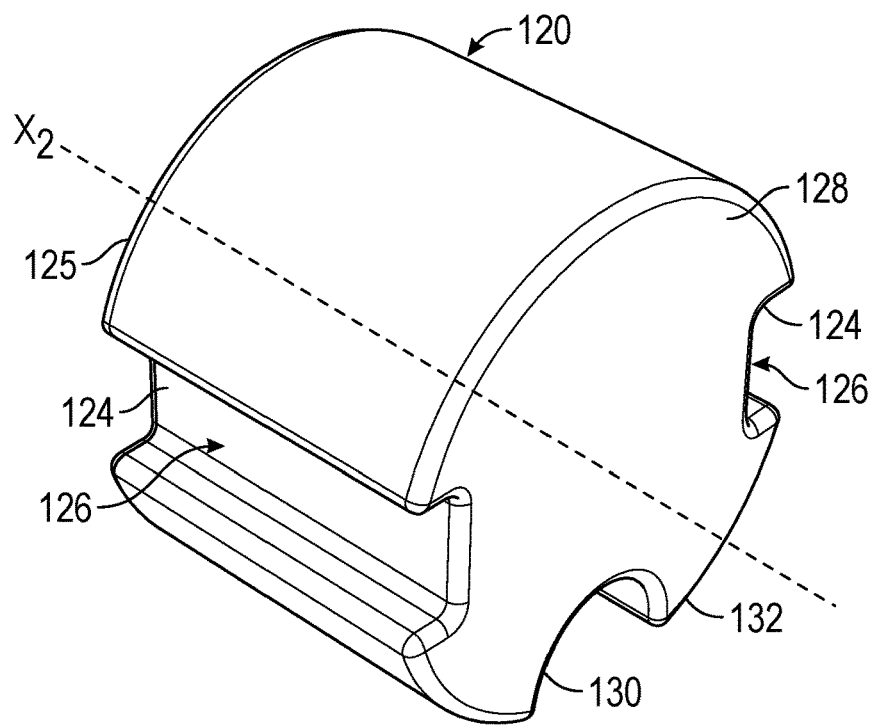
FIG. 2D illustrates a perspective view of a valve member of the flow control device of FIG. 2A in accordance with some embodiments.

FIG. 2D illustrates a perspective view of a valve member of the flow control device of FIG. 2A in accordance with some embodiments. As illustrated in FIG. 2D, and with continued reference to FIG. 2C, the valve member 120 may be in the form of a cylindrical disc, which is slidably mounted in the chamber 114. To this effect, the valve member 120 may have at least one slot 124 extending longitudinally along an outer circumferential surface 132 of the valve member 120. As depicted, the slot 124 may define a recess 126 having a shape corresponding to that of the guide rail 122 for mounting the valve member 120 onto the guide rail 122.

In some embodiments, the valve member 120 may have more than one slot, for example two slots 124 symmetrically disposed about the central longitudinal axis $X_2$ of the valve member 120. As such, the valve member 120 may be mounted on the inner circumferential surface 116 with the rail(s) 122 engaged in the recess(es) 126 of the slot(s) 124. Accordingly, when the valve member 120 is subject to fluid pressure from either of the primary IV line 5 or the secondary IV line 7, the valve member 120 may be translated or otherwise displaced within the chamber 114 along the length of the guide rails 122. The aforementioned configuration is advantageous as the engagement between the guide rails 122 and slots 124 restrain degrees of movement of the valve member 120 in the chamber 114. In particular, the aforementioned configuration acts as an anti-rotation mechanism to prevent the valve member 120 from rolling or rotating about the central axis X of the housing 102.

Figure 2F:
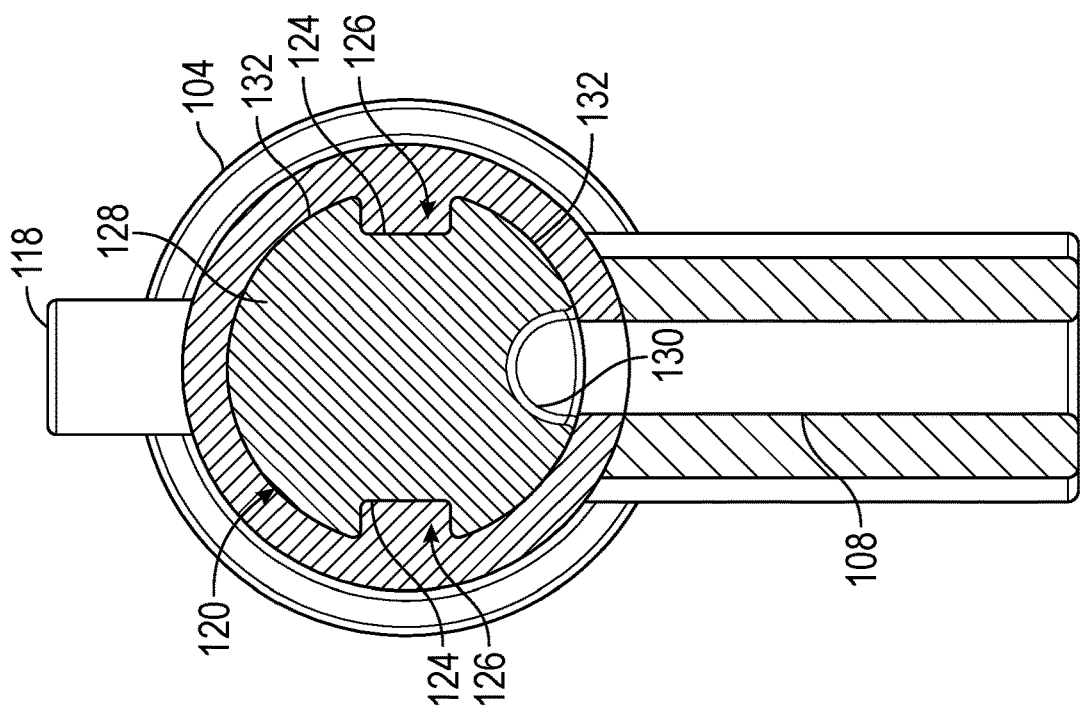
FIG. 2F illustrates a cross-sectional view of a housing and mounted valve member of a flow control device, in accordance with some embodiments of the present disclosure.
Figure 2E:
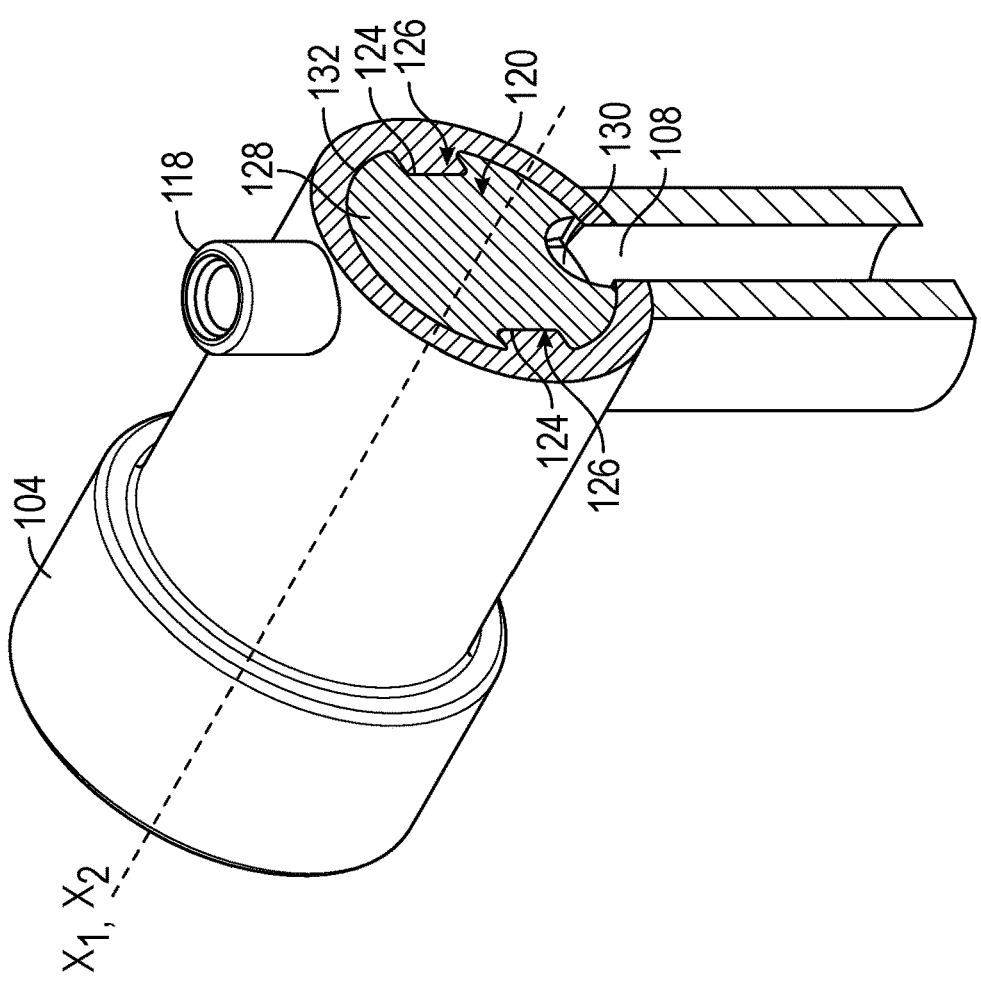
FIG. 2E illustrates a partial cross-sectional view of a housing and mounted valve member of a flow control device, in accordance with some embodiments of the present disclosure.

FIG. 2E illustrates a partial cross-sectional view of a housing 102 and mounted valve member 120 of a flow control device 100, in accordance with some embodiments of the present disclosure. FIG. 2F illustrates a cross-sectional view of a housing 102 and mounted valve member 120 of a flow control device 100, in accordance with some embodiments of the present disclosure. In some embodiments, the valve member 120 may further include a flow groove 130 extending longitudinally (e.g., linearly) from a planar surface 128 of the valve member 120. The flow groove 130 may extend longitudinally along an outer circumferential surface 132 of the valve member 120. As depicted, the flow groove 130 may extend only partially along the length of the valve member 120. Accordingly, the flow groove 130 may serve to fluidly communicate the secondary inlet 112 with the outlet 108 when fluid pressure at the primary inlet 106 is equal to fluid pressure at the secondary inlet 112.

FIG. 3A is a cross-sectional view illustrating a flow control device and valve member before coupling to fluid lines of an IV set, in accordance with some embodiments of the present disclosure. FIG. 3A illustrates a condition of the flow control device 100 when initially packaged, before being utilized in an IV set. FIG. 3B is a cross-sectional view illustrating the flow control device and valve member of FIG. 3A when coupled to primary and secondary fluid lines of an IV set, where fluid pressure in the primary line is higher than that in the secondary line, in accordance with some embodiments of the present disclosure.

Referring to FIG. 3B, in operation, when subject to a net primary fluid pressure (i.e., a pressure applied by a fluid flowing from the primary inlet 106 towards the chamber 114 that exceeds that of any pressure applied by fluid in the secondary IV line), the valve member 120 may be translated towards the secondary inlet 112 to a position where the planar surface 128 of the valve member contacts and blocks the secondary inlet 112. Accordingly, fluid flow from the secondary IV line 7 into the chamber 114 may be blocked, and only fluid from the primary IV line 5 may flow into the chamber 114 via the primary inlet 106. The fluid from the primary IV line 5 may thus be delivered to the patient 50 through the outlet 108.

FIG. 3C is a cross-sectional view illustrating the flow control device and valve member of FIG. 3A when coupled to primary and secondary fluid lines of an IV set, where fluid pressure in the secondary line is higher than that in the primary line, in accordance with some embodiments of the present disclosure.

Referring to FIG. 3C, in operation, when subject to a net secondary fluid pressure (i.e., a pressure applied by a fluid flowing from the secondary inlet 112 towards the chamber 114 that exceeds that of any pressure applied by fluid in the primary IV line), the valve member 120 may be translated towards the primary inlet 106 to a position where the surface 125 of the valve member contacts and blocks the secondary inlet 112. Accordingly, fluid flow from the primary IV line 5 into the chamber 114 may be blocked, and only fluid from the secondary IV line 7 may flow into the chamber 114 via the secondary inlet 112. The fluid from the secondary IV line 7 may thus be delivered to the patient 50 through the outlet 108.

Figure 3D:
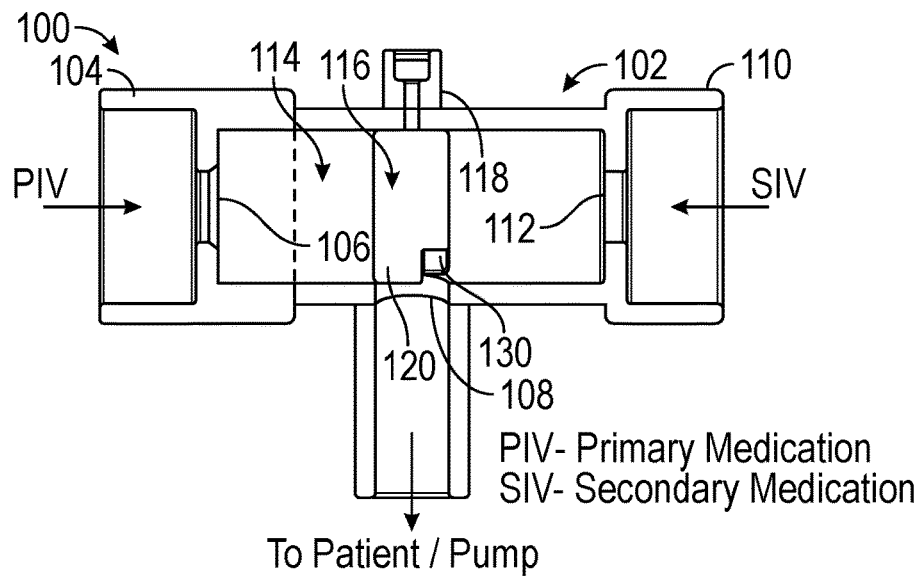
FIG. 3D is a cross-sectional view illustrating the flow control device and valve member of FIG. 3A when coupled to primary and secondary fluid lines of an IV set, where fluid pressure in the primary line equals that in the secondary line, in accordance with some embodiments of the present disclosure.
Figure 3E:
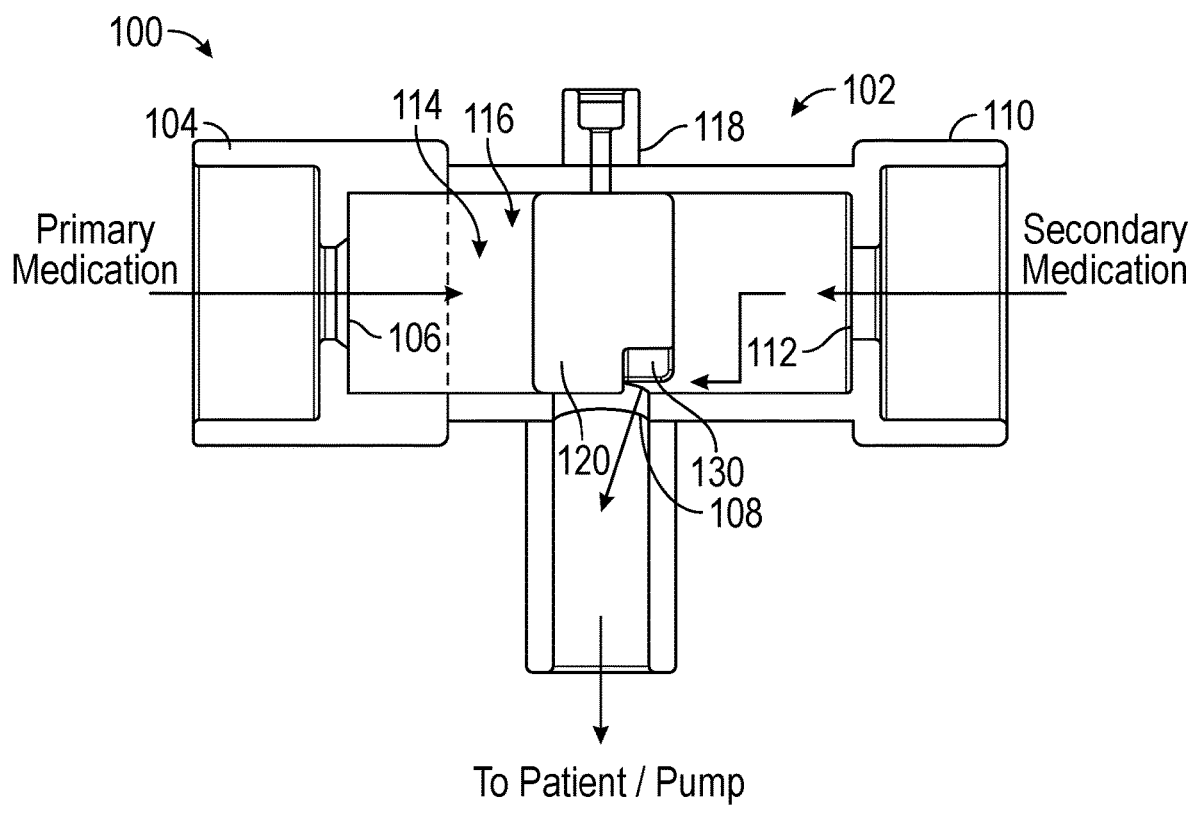
FIG. 3E is a cross-sectional view illustrating the flow control device and valve member of FIG. 3D, where a flow groove profile of the valve member allows fluid to flow from a secondary fluid line to the outlet port when fluid pressure in the primary line equals that in the secondary line, in accordance with some embodiments of the present disclosure.

FIGS. 3D and 3E are cross-sectional views illustrating the flow control device and valve member of FIG. 3A when coupled to primary and secondary fluid lines of an IV set, where fluid pressure in the primary line equals that in the secondary line, in accordance with some embodiments of the present disclosure.

Referring to FIGS. 3D and 3E, in operation, when subject to a primary fluid pressure that equals that of a secondary fluid pressure (i.e., a pressure applied by a fluid flowing from the primary IV line 5 into the primary inlet 106 that equals pressure applied by fluid flowing from the secondary IV line 7 into the secondary inlet 112), the valve member 120 may be translated towards a central portion of the chamber 114 just above the outlet 108. Since the fluid pressure at the primary inlet equals the fluid pressure at the secondary inlet, the position of the valve member 120 may be equidistant from the primary and secondary inlets 106 and 112. At this position just above the outlet, the flow groove 130 of the valve member may allow fluid to flow from the secondary IV line 7 into the chamber 114 via the secondary inlet 112. Accordingly, when fluid pressure in the primary and secondary IV lines 5 and 7 is equal, only the secondary medication may be dispensed to the patient via the flow groove 130. Since the surface 125 has no flow groove, fluid communication between the primary inlet and the outlet is blocked, thereby stopping the fluid in the IV line from being dispensed to the patient.

Figure 4:
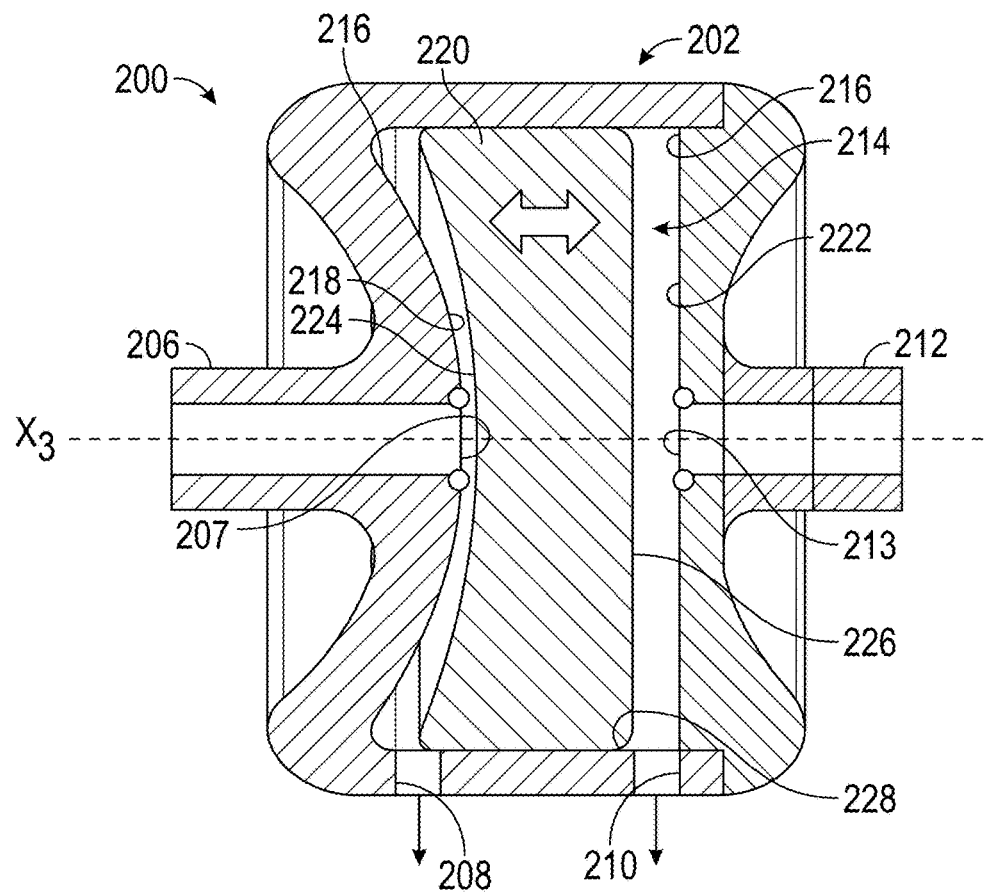
FIG. 4 illustrates a cross-sectional view of a flow control device, in accordance with some embodiments of the present disclosure.

FIG. 4 illustrates a cross-sectional view of a flow control device 200, in accordance with some embodiments of the present disclosure. In some embodiments, the flow control device 200 may have a housing 202 including a primary inlet 212, a primary outlet 210, a secondary inlet 206, a secondary outlet 208, and a chamber 214 interposed between the primary and secondary inlets 212 and 206. The flow control device 200 may further include a valve member 220 reciprocally mounted in the chamber 214. The primary and secondary outlets 210 and 208 may define a fluid path through which medication or drugs from the primary and secondary inlets 212 and 206 may be delivered to the patient 50. The primary and secondary inlets 212 and 206 may share a common central axis $X_3$. The primary inlet 212 may fluidly communicate the primary IV line 5 with the chamber 214. Similarly, the secondary inlet 206 may fluidly communicate the secondary IV line 7 with the chamber 214. The primary and secondary outlets 210 and 208 may each have a central axis, and each of the central axes may be perpendicularly disposed relative to the common central axis $X_3$ of the primary and secondary inlets 212 and 206.

Referring to FIG. 4, the flow control device 200 is displayed in cross-sectional view to more clearly illustrate some of the features of the valve member 220. As depicted, the flow control device 200 may be in the form of a generally cylindrical (or tubular) body or may have any other shape with a hollow interior capable of defining the chamber 214. Similar to the embodiments previously described, the chamber 214 may be defined by an inner circumferential surface 216 of the housing 202. As depicted, the chamber 214 may extend between the primary and secondary inlets 212 and 206 to fluidly connect the primary and secondary inlets 212 and 206 with the respective primary and secondary outlets 210 and 208.

In some embodiments, the inner circumferential surface 216 may include a primary sealing surface 222 defining an inlet port 213 of the primary inlet 212 and a secondary sealing surface 218 defining an inlet port 207 of the secondary inlet 206. As shall be described in further detail below, the primary and secondary sealing surfaces 222 and 218 may be structured specifically so as to correspond to a structure of the valve member 220 in order for the valve member to seal the primary inlet port 213 and the secondary inlet port 207 respectively.

As illustrated, the valve member 220 may be in the form of a disc having a primary inlet sealing surface 226 corresponding to the primary sealing surface 222 of the housing 202. Similarly, the valve member 220 may include a secondary inlet sealing surface 224 corresponding to the secondary sealing surface 218 of the housing. Additionally, the valve member 220 may include an outlet sealing surface 228 for selectively sealing the primary and secondary outlets 210 and 208.

In operation, when subject to a net primary fluid pressure (i.e., a pressure applied by a fluid flowing from the primary inlet 212 towards the chamber 214 that exceeds that of any pressure applied by fluid in the secondary IV line 7), the valve member 220 may be translated towards the secondary inlet 206. As the valve member moves towards the secondary inlet 206 and away from the primary inlet 212, the primary inlet port 213 and the primary outlet 210 may be opened. Fluid from the primary IV line 5 may then flow into the chamber 214 via the primary inlet 212 and be dispensed to the patient via the primary outlet 210. When the valve member 220 is translated to a position where the secondary inlet sealing surface 224 of the valve member 220 contacts the secondary sealing surface 218, both the secondary inlet port 207 and the secondary outlet 208 may be occluded by the valve member 220.

In order for the secondary inlet sealing surface 224 of the valve member 220 to contact and seal the secondary inlet port 207, the secondary inlet sealing surface 224 and the secondary sealing surface 218 may have complimentary profiles. For example, the secondary inlet sealing surface 224 and the secondary sealing surface 218 may have non-planar profiles. As depicted, the secondary inlet sealing surface 224 may have a curved profile, for example, but not limited to, a concave profile. Accordingly, the secondary sealing surface 218 may have a complimentary curved profile, for example, but not limited to, a convex profile.

At the position where the secondary inlet sealing surface 224 of the valve member 220 contacts and seals the secondary inlet port 207, fluid flow from the secondary IV line 7 into the chamber 214 is blocked. Accordingly, only fluid (e.g., primary drug) from the primary IV line 5 may be dispensed to the patient 50 via the primary inlet port 213 and the primary outlet 210.

When subject to a net secondary fluid pressure (i.e., a pressure applied by a fluid flowing from the secondary inlet 206 towards the chamber 214 that exceeds that of any pressure applied by fluid in the primary IV line 5), the valve member 220 may be translated towards the primary inlet port 213. As previously discussed, the secondary inlet sealing surface 224 and the secondary sealing surface 218 may have complimentary non-planar profiles. In particular, as depicted, the secondary inlet sealing surface 224 may have a concave profile and the secondary sealing surface 218 may have a complimentary convex profile. The aforementioned configuration is advantageous in that the curved profile of the secondary inlet sealing surface 224 of valve member 220 would be subject to a lower drag force than if the surface 224 was a flat or planar surface. Accordingly, a lower fluid pressure threshold at the inlet port 207 would be required to move the valve member 220 away from the inlet port 207 so that fluid could flow from the secondary IV line into the chamber 214 for dispensing to the patient via the outlet 208.

As the valve member 220 continues to move towards the primary inlet 212 and away from the secondary inlet 206, the secondary inlet port 207 and the secondary outlet 208 may be opened. Fluid from the secondary IV line 7 may then flow into the chamber 214 via the secondary inlet 206 and be dispensed to the patient 50 via the secondary outlet 208. When the valve member 220 is translated to a position where the primary inlet sealing surface 226 of the valve member 220 contacts the primary sealing surface 222, both the primary inlet port 213 and the primary outlet 210 may be occluded by the valve member 220.

In order for the primary inlet sealing surface 226 of the valve member 220 to contact and seal the primary inlet port 213, the primary inlet sealing surface 226 and the primary sealing surface 222 may have complimentary profiles. For example, the primary inlet sealing surface 226 and the primary sealing surface 222 may have matching or complimentary planar profiles. As depicted, the primary inlet sealing surface 226 may have a flat profile and the primary sealing surface 222 may have a complimentary flat profile.

However, the various embodiments of the present disclosure are not limited to the aforementioned configuration. In some embodiments, similar to the secondary inlet sealing surface 224 and the secondary sealing surface 218, the primary inlet sealing surface 226 and the primary sealing surface 222 may have complimentary non-planar profiles.

At the position where the primary inlet sealing surface 226 of the valve member 220 contacts and seals the primary inlet port 213, fluid flow from the primary IV line 7 into the chamber 214 is blocked. Accordingly, only fluid (e.g., secondary drug) from the secondary IV line 7 may be dispensed to the patient 50 via the secondary inlet port 207 and the secondary outlet 208. Accordingly, backflow of fluid from the secondary IV line 7 into the primary IV line 5 is prevented. Similarly, under-infusion of the secondary drug—which commonly occurs as a result of the secondary drug flowing into the primary IV line 5 from the chamber 214—may be prevented. Preventing backflow of the fluid is advantageous in that it restricts undesirable particulate matter (for example, contained in the drug dispensed from the secondary IV line 7) from flowing back through the valve member 220, and thereby preventing the patient 50 from receiving the proper drug dosage concentration or from timely delivery of the drug.

Figure 5:
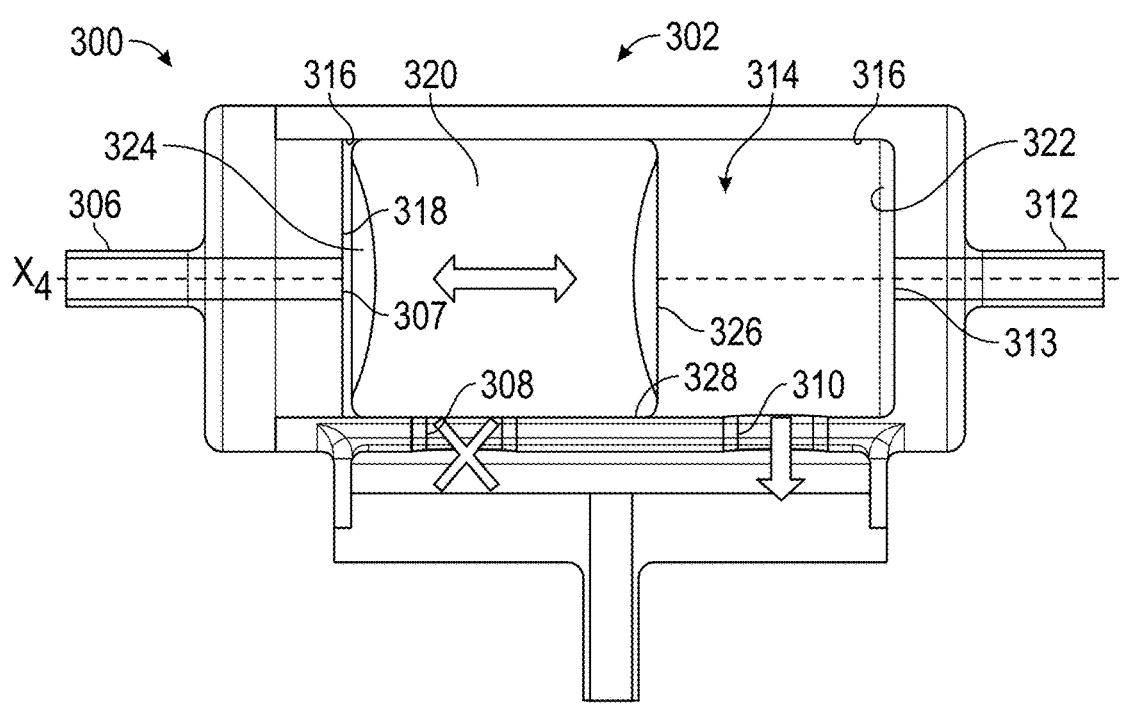
FIG. 5 illustrates a cross-sectional view of a flow control device, in accordance with some embodiments of the present disclosure.

FIG. 5 illustrates a cross-sectional view of a flow control device 300, in accordance with some embodiments of the present disclosure. In some embodiments, the flow control device 300 may have a housing 302 including a primary inlet 312, a primary outlet 310, a secondary inlet 306, a secondary outlet 308, and a chamber 314 interposed between the primary and secondary inlets 312 and 306. The flow control device 300 may further include a valve member 320 reciprocally mounted in the chamber 314. The primary and secondary outlets 310 and 308 may define a fluid path through which medication or drugs from the primary and secondary inlets 312 and 306 may be delivered to the patient 50. The primary and secondary inlets 312 and 306 may share a common central axis $X_4$. The primary inlet 312 may fluidly communicate the primary IV line 5 with the chamber 314. Similarly, the secondary inlet 306 may fluidly communicate the secondary IV line 7 with the chamber 314. The primary and secondary outlets 310 and 308 may each have a central axis, and each of the central axes may be perpendicularly disposed relative to the common central axis $X_4$ of the primary and secondary inlets 312 and 306.

Referring to FIG. 5, the flow control device 300 is displayed in cross-sectional view to more clearly illustrate some of the features of the valve member 320. As depicted, the flow control device 300 may be in the form of a generally cylindrical (or tubular) body or may have any other shape with a hollow interior capable of defining the chamber 314. Similar to the embodiments previously described, the chamber 314 may be defined by an inner circumferential surface 316 of the housing 302. As depicted, the chamber 314 may extend between the primary and secondary inlets 312 and 306 to fluidly connect the primary and secondary inlets 312 and 306 with the respective primary and secondary outlets 310 and 308.

In some embodiments, the inner circumferential surface 316 may include a primary sealing surface 322 defining an inlet port 313 of the primary inlet 312 and a secondary sealing surface 318 defining an inlet port 307 of the secondary inlet 306. As shall be described in further detail below, the primary and secondary sealing surfaces 322 and 318 may be structured specifically so as to correspond to a structure of the valve member 320 in order for the valve member to seal the primary inlet port 313 and the secondary inlet port 307 respectively.

As illustrated, the valve member 320 may be in the form of a disc having a primary inlet sealing surface 326 corresponding to the primary sealing surface 322 of the housing 302. Similarly, the valve member 320 may include a secondary inlet sealing surface 324 corresponding to the secondary sealing surface 318 of the housing 302. Additionally, the valve member 320 may include an outlet sealing surface 328 for selectively sealing the primary and secondary outlets 310 and 308.

In operation, when subject to a net primary fluid pressure (i.e., a pressure applied by a fluid flowing from the primary inlet 312 towards the chamber 314 that exceeds that of any pressure applied by fluid in the secondary IV line 7), the valve member 320 may be translated towards the secondary inlet 306. As the valve member moves towards the secondary inlet 306 and away from the primary inlet 312, the primary inlet port 313 and the primary outlet 310 may be opened. Fluid from the primary IV line 5 may then flow into the chamber 314 via the primary inlet 312 and be dispensed to the patient via the primary outlet 310. When the valve member 320 is translated to a position where the secondary inlet sealing surface 324 of the valve member 320 contacts the secondary sealing surface 318, both the secondary inlet port 307 and the secondary outlet 308 may be occluded by the valve member 320.

In some embodiments, in order for the secondary inlet sealing surface 324 of the valve member 320 to contact and seal the secondary inlet port 307, the secondary inlet sealing surface 324 and the secondary sealing surface 318 may have complimentary profiles. For example, the secondary inlet sealing surface 324 and the secondary sealing surface 318 may have complimentary non-planar profiles. As depicted, the secondary inlet sealing surface 324 may have a curved profile, for example, but not limited to, a concave profile. Accordingly, the secondary sealing surface 318 may have a complimentary curved profile, for example, but not limited to, a convex profile.

At the position where the secondary inlet sealing surface 324 of the valve member 320 contacts and seals the secondary inlet port 307, fluid flow from the secondary IV line 7 into the chamber 314 is blocked. Accordingly, only fluid (e.g., primary drug) from the primary IV line 5 may be dispensed to the patient 50 via the primary inlet port 313 and the primary outlet 310.

When subject to a net secondary fluid pressure (i.e., a pressure applied by a fluid flowing from the secondary inlet 306 towards the chamber 314 that exceeds that of any pressure applied by fluid in the primary IV line 5), the valve member 320 may be translated towards the primary inlet port 313. As previously discussed, the secondary inlet sealing surface 324 and the secondary sealing surface 318 may have complimentary non-planar profiles. In particular, the secondary inlet sealing surface 324 may have a concave profile and the secondary sealing surface 318 may have a complimentary convex profile. The aforementioned configuration is advantageous in that the curved profile of the secondary inlet sealing surface 324 of valve member 320 would be subject to a lower drag force than if the surface 324 was a flat or planar surface. Accordingly, a lower fluid pressure threshold at the inlet port 307 would be required to move the valve member 320 away from the inlet port 307 so that fluid could flow from the secondary IV line 7 into the chamber 314 for dispensing to the patient via the outlet 308.

As the valve member 320 continues to move towards the primary inlet 312 and away from the secondary inlet 306, the secondary inlet port 307 and the secondary outlet 308 may be opened. Fluid from the secondary IV line 7 may then flow into the chamber 314 via the secondary inlet 306 and be dispensed to the patient 50 via the secondary outlet 308. When the valve member 320 is translated to a position where the primary inlet sealing surface 326 of the valve member 320 contacts the primary sealing surface 322, both the primary inlet port 313 and the primary outlet 310 may be occluded by the valve member 320.

In order for the primary inlet sealing surface 326 of the valve member 320 to contact and seal the primary inlet port 313, the primary inlet sealing surface 326 and the primary sealing surface 322 may have complimentary profiles. For example, the primary inlet sealing surface 326 and the primary sealing surface 322 may have matching or complimentary planar profiles. As depicted, the primary inlet sealing surface 326 may have a flat profile and the primary sealing surface 322 may have a complimentary flat profile. However, the various embodiments of the present disclosure are not limited to the aforementioned configuration. In some embodiments, similar to the secondary inlet sealing surface 324 and the secondary sealing surface 318, the primary inlet sealing surface 326 and the primary sealing surface 322 may have complimentary non-planar profiles.

At the position where the primary inlet sealing surface 326 of the valve member 320 contacts and seals the primary inlet port 313, fluid flow from the primary IV line 7 into the chamber 314 is blocked. Accordingly, only fluid (e.g., secondary drug) from the secondary IV line 7 may be dispensed to the patient 50 via the secondary inlet port 307 and the secondary outlet 308. Accordingly, backflow of fluid from the secondary IV line 7 into the primary IV line 5 is restricted or prevented. Similarly, under-infusion of the secondary drug—which commonly occurs as a result of the secondary drug flowing into the primary IV line 5 from the chamber 314—may be prevented. Preventing backflow of the fluid is advantageous in that it restricts undesirable particulate matter (for example, contained in the drug dispensed from the secondary IV line 7) from flowing back through the valve member 320, and thereby preventing the patient 50 from receiving the proper drug dosage concentration or from timely delivery of the drug.

In operation, when subject to a primary fluid pressure that equals that of a secondary fluid pressure (i.e., a pressure applied by a fluid flowing from the primary IV line 5 into the primary inlet 312 that equals pressure applied by fluid flowing from the secondary IV line 7 into the secondary inlet 306), the valve member 320 may be translated towards a central portion of the chamber 314 between the primary and secondary outlets 310 and 308. Since the fluid pressure at the primary inlet 312 equals the fluid pressure at the secondary inlet 306, the position of the valve member 320 may be equidistant from each of the primary and secondary inlets ports 313 and 307. At this position both the primary inlet port 313 and primary outlet 310, and the secondary inlet port 307 and secondary outlet 308 are open allowing fluid to flow equally from both of the primary and secondary IV lines 5 and 7 to the patient 50. Accordingly, given the aforementioned configuration, a primary drug and a secondary drug may be administered in equal proportions to the patient without the possibility of backflow of drug from one IV fluid line into the other.

Accordingly, the various embodiments of the present disclosure are advantageous in providing a flow control device capable of preventing under-infusion of the secondary drug by blocking the secondary drug from flowing backwards into the primary IV line, as discussed previously. The flow control device of the various embodiments described herein is further advantageous as it minimizes the number of separate components of an IV set by replacing a check valve and a y-connector with the single flow control device. As a result, cost of the IV set may be reduced. Additionally, the various embodiments of the present disclosure are advantageous in reducing workflow steps for the clinician/nurses since no manual operation is necessary for flow regulation as the flow pressure of the secondary drug or fluid is used to regulate flow of the primary drug or fluid.

The present disclosure is provided to enable any person skilled in the art to practice the various aspects described herein. The disclosure provides various examples of the subject technology, and the subject technology is not limited to these examples. Various modifications to these aspects will be readily apparent to those skilled in the art, and the generic principles defined herein may be applied to other aspects.

A reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

The word "exemplary" is used herein to mean "serving as an example or illustration." Any aspect or design described herein as "exemplary" is not necessarily to be construed as preferred or advantageous over other aspects or designs. In one aspect, various alternative configurations and operations described herein may be considered to be at least equivalent.

As used herein, the phrase "at least one of" preceding a series of items, with the term "or" to separate any of the items, modifies the list as a whole, rather than each item of the list. The phrase "at least one of" does not require selection of at least one item; rather, the phrase allows a meaning that includes at least one of any one of the items, and/or at least one of any combination of the items, and/or at least one of each of the items. By way of example, the phrase "at least one of A, B, or C" may refer to: only A, only B, or only C; or any combination of A, B, and C.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

In one aspect, unless otherwise stated, all measurements, values, ratings, positions, magnitudes, sizes, and other specifications that are set forth in this specification, including in the claims that follow, are approximate, not exact. In one aspect, they are intended to have a reasonable range that is consistent with the functions to which they relate and with what is customary in the art to which they pertain.

It is understood that the specific order or hierarchy of steps, or operations in the processes or methods disclosed are illustrations of exemplary approaches. Based upon implementation preferences or scenarios, it is understood that the specific order or hierarchy of steps, operations or processes may be rearranged. Some of the steps, operations or processes may be performed simultaneously. In some implementation preferences or scenarios, certain operations may or may not be performed. Some or all of the steps, operations, or processes may be performed automatically, without the intervention of a user. The accompanying method claims present elements of the various steps, operations or processes in a sample order, and are not meant to be limited to the specific order or hierarchy presented.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112 (f) unless the element is expressly recited using the phrase "means for" or, in the case of a method claim, the element is recited using the phrase "step for." Furthermore, to the extent that the term "include," "have," or the like is used, such term is intended to be inclusive in a manner similar to the term "comprise" as "comprise" is interpreted when employed as a transitional word in a claim.

The Title, Background, Summary, Brief Description of the Drawings and Abstract of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in each claim. Rather, as the following claims reflect, inventive subject matter lies in less than all features of a single disclosed configuration or operation. The following claims are hereby incorporated into the Detailed Description, with each claim standing on its own as a separately claimed subject matter.

The claims are not intended to be limited to the aspects described herein, but are to be accorded the full scope consistent with the language of the claims and to encompass all legal equivalents. Notwithstanding, none of the claims are intended to embrace subject matter that fails to satisfy the requirement of 35 U.S.C. § 101, 102, or 103, nor should they be interpreted in such a way.

What is claimed is:

1. A flow control device, comprising:
   a housing including a primary inlet, a primary outlet, a secondary inlet, and a secondary outlet, wherein the primary and secondary inlets share a common central axis that is perpendicularly disposed relative to central axes of the primary and secondary outlets;
   a chamber defined by an inner circumferential surface of the housing, the chamber extending between the primary and secondary inlets for fluidly connecting the primary inlet with the primary outlet and the secondary inlet with the secondary outlet; and
   a valve member reciprocally mounted in the chamber to (i) block fluid communication between the secondary inlet and the secondary outlet when fluid pressure into the primary inlet is higher than fluid pressure into the secondary inlet, and (ii) block fluid communication between the primary inlet and the primary outlet when fluid pressure into the secondary inlet is higher than fluid pressure into the primary inlet,
   wherein the inner circumferential surface includes a primary sealing surface defining an inlet port of the primary inlet and a secondary sealing surface defining an inlet port of the secondary inlet, and
   the valve member comprises a disc having a primary inlet sealing surface corresponding to the primary sealing surface, a secondary inlet sealing surface corresponding to the secondary sealing surface, and an outlet sealing surface for selectively sealing the primary and secondary outlets.

2. The flow control device of claim 1, wherein the primary inlet sealing surface comprises a planar profile and the secondary inlet sealing surface comprises a non-planar profile.

3. The flow control device of claim 2, wherein the secondary inlet sealing surface of the valve member comprises a curved profile.

4. The flow control device of claim 2, wherein the secondary inlet sealing surface of the valve member comprises a concave profile.

5. The flow control device of claim 1, wherein the primary sealing surface of the housing comprises a planar profile and the secondary sealing surface of the housing comprises a non-planar profile.

6. The flow control device of claim 5, wherein the secondary sealing surface of the housing comprises a curved profile.

7. The flow control device of claim 5, wherein the secondary sealing surface of the housing comprises a convex profile.

8. The flow control device of claim 1, wherein the valve member is configured to allow fluid communication between the primary inlet and the primary outlet and between the secondary inlet and the secondary outlet when the fluid pressure into the primary inlet is equal to the fluid pressure into the secondary inlet.

9. The flow control device of claim 1, wherein at least one of the primary inlet sealing surface and the secondary inlet sealing surface comprises a non-planar profile.

10. The flow control device of claim 1, wherein the primary outlet and the secondary outlet are fluidly coupled to a combined outlet.

* * * * *